(12) United States Patent
Pasquier et al.

(10) Patent No.: US 7,429,274 B2
(45) Date of Patent: Sep. 30, 2008

(54) AGENT AND METHOD FOR THE OXIDATIVE COLORING OF KERATIN FIBERS

(75) Inventors: Cecile Pasquier, Marly (CH); Veronique Buclin, Morlon (CH); Caroline Kiener, Marly (CH); Nadja Duc-Reichlin, Lully (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 176 days.

(21) Appl. No.: 10/581,066

(22) PCT Filed: Nov. 15, 2004

(86) PCT No.: PCT/EP2004/012941

§ 371 (c)(1),
(2), (4) Date: May 31, 2006

(87) PCT Pub. No.: WO2005/060927

PCT Pub. Date: Jul. 7, 2005

(65) Prior Publication Data

US 2007/0079452 A1    Apr. 12, 2007

(30) Foreign Application Priority Data

Dec. 16, 2003  (DE) ................ 103 58 883

(51) Int. Cl.
*A61Q 5/10*  (2006.01)
*C07D 277/04*  (2006.01)
(52) U.S. Cl. .............. 8/405; 8/406; 8/408; 8/573; 8/575; 8/576; 548/146
(58) Field of Classification Search ............. 8/405, 8/406, 408, 409, 573, 575, 576; 548/146
See application file for complete search history.

(56) References Cited

U.S. PATENT DOCUMENTS 3,634,013 A    1/1972  Rudolf

FOREIGN PATENT DOCUMENTS

| AT | 282072 | 6/1970 |
| DE | 1 049 381 | 1/1959 |
| DE | 1 922 400 | 12/1969 |
| DE | 101 14 426 | 9/2002 |
| WO | 02/074268 | 9/2002 |
| WO | WO 02/074268 A2 * | 9/2002 |

OTHER PUBLICATIONS

Research Disclosure 174, Oct. 1978, pp. 42-44 (In English).

* cited by examiner

*Primary Examiner*—Eisa B Elhilo
(74) *Attorney, Agent, or Firm*—Michael J. Striker

(57) ABSTRACT

The object of the present invention is a ready-to-use agent for coloring keratin fibers containing (i) at least one heterocyclic hydrazone derivative of formula (I), (ii) at least one CH-active compound of formulas (II) to (IX) and (iii) at least one oxidant, a multicomponent kit and a method for coloring keratin fibers by use of said agent.

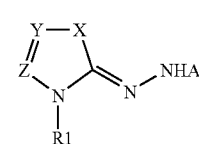

(I)

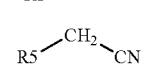

(II)

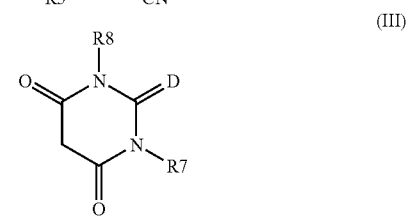

(III)

(IV)

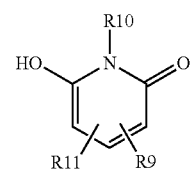

(V)

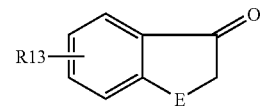

(VI)

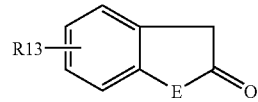

(VII)

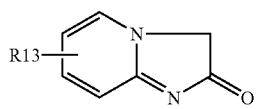

(VIII)

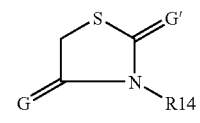

(IX)

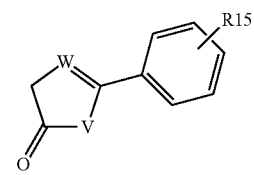

15 Claims, No Drawings

AGENT AND METHOD FOR THE OXIDATIVE COLORING OF KERATIN FIBERS

CROSS-REFERENCE

This is the U.S. National Stage of PCT/EP 2004/012941, filed on Nov. 15, 2004 in the European Patent Office.

BACKGROUND OF THE INVENTION

The present application has for an object a ready-to-use agent for coloring keratin fibers, for example silk, wool or hair and particularly human hair, said agent containing (i) a heterocyclic hydrazone derivative, (ii) a —CH-active compound and (iii) an oxidant and furthermore a multicomponent kit and a method for coloring keratin fibers by use of said colorant.

Hair colorants are divided mainly into the groups of oxidation colorants and tinting agents, depending on the starting hair to be colored and the desired result. Oxidation colorants are eminently suited for covering large gray areas, the oxidation colorants used for gray areas of up to 50% are usually referred to as oxidative tinting agents, whereas the oxidation colorants used for gray areas of more than 50% or for "brightening" are usually referred to as oxidative colorants. Direct dyes are contained primarily in non-oxidative colorants (tinting agents). Because of their small molecular size, some direct dyes, for example nitro dyes, can penetrate into the hair and dye it directly, at least in the outer regions. Such tinting is very gentle to the hair and as a rule can withstand 6 to 8 hair washings. Direct dyes are frequently used also in oxidative colorants for producing certain shades or to intensify the color.

DE-A 1 922 400 discloses the use of hydrazones for coloring keratin fibers. These colorants, however, cannot meet the requirements placed on colorants in every respect, particularly as regards the luster and intensity of the colorations.

SUMMARY OF THE INVENTION

Surprisingly, we have now found that intense and bright colorations are obtained by use of a combination of certain heterocyclic hydrazones and certain CH-active compounds in the presence of an oxidant.

Hence, the present invention has for an object a ready-to-use agent for coloring keratin fibers, for example wool, silk or hair and particularly human hair, characterized in that it contains (a) at least one hydrazone derivative of formula (I) or a physiologically compatible salt thereof:

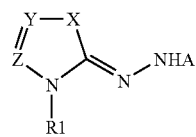

(I)

wherein
X stands for oxygen, sulfur or NR2,
Y stands for C—R3 or nitrogen and
Z stands for C—R4 or nitrogen, provided that the heterocyclic part of the compound of formula (I) contains at the most three heteroatoms;

A stands for hydrogen, an acetyl group, a trifluoroacetyl group, a formyl group, a ($C_1$-$C_6$)-alkylsulfonyl group or an arylsulfonyl group;

R1 and R2 can be equal or different and independently of each other denote a saturated or unsaturated ($C_1$-$C_{12}$)-alkyl group, a halogen (F, Cl, Br, I)-substituted ($C_1$-$C_2$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a —C(CO)—($C_1$-$C_{12}$)-alkyl group, a substituted or unsubstituted —C(O)-phenyl group, a —C(O)NH—($C_1$-$C_{12}$)-alkyl group, a substituted or unsubstituted —C(O)NH-phenyl group, a substituted or unsubstituted phenyl group or a benzyl group;

R3 and R4 can be identical or different and independently of each other denote hydrogen, a halogen atom (F, Cl, Br, I), a saturated or unsaturated ($C_1$-$C_{12}$)-alkyl group, a halogen atom (F, Cl, Br, I)-substituted ($C_1$-$C_{12}$)-alkyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a di($C_{1-C12}$)-alkylamino group, a carboxyl group, a —C(O)O—($C_{1-C12}$)-alkyl group, a substituted or unsubstituted —C(O)O-phenyl group, a substituted or unsubstituted phenyl phenyl group or a naphthyl group;

and when Y and Z stand for C—R3 and C—R4, R3 and R4 together with the remainder of the molecule can form a heterocyclic or carbocyclic, saturated or unsaturated, substituted or unsubstituted ring system;

(b) at least one CH-active compound of formulas (II) to (IX) with

(II)

wherein R5 denotes a cyano group, a (CO)—R6 carbonyl function, with R6 denoting a ($C_{1-C12}$)-alkoxy group, an amino group, a ($C_1$-$C_{12}$)-alkylamino group, an arylamino group, ($C_1$-$C_{12}$)-alkyl group or an aryl group;

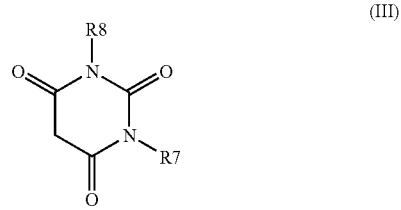

(III)

wherein R7 and R8 can be equal or different and denote hydrogen, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_2$-$C_6$)-alkyl group, an amino-($C_1$-$C_{12}$)-alkyl group, or a carbocyclic or heterocyclic, substituted or unsubstituted aromatic compound, and D stands for a sulfur atom or oxygen atom;

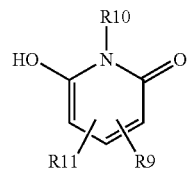
(IV)

wherein R9 denotes a hydrogen atom, a nitrile group, a ($C_1$-$C_{12}$)-alkyl group, a carbocyclic or heterocyclic aromatic compound or a (CO)—R12 carbonyl function, within R12 standing for hydrogen, a hydroxyl group, a ($C_1$-$C_{12}$)-alkoxy group, an amino group, a ($C_1$-$C_{12}$)-alkylamino group, a ($C_1$-$C_{12}$)-alkyl group or an aryl group, and R10 and R 11 can be equal or different and independently of each other denote hydrogen, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_2$-$C_6$)-alkyl group, an amino-($C_1$-$C_{12}$)-alkyl group, or a carbocyclic or heterocyclic aromatic compound;

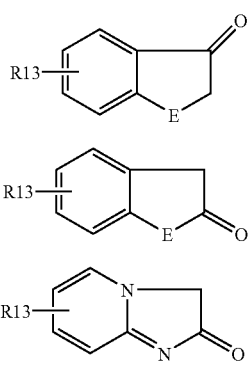
(V)
(VI)
(VII)

wherein E denotes an oxygen atom, a sulfur atom of an NR' amino group, with R' standing for hydrogen or a substituted or unsubstituted ($C_1$-$C_{12}$)-alkyl group, and R13 stands for a hydrogen atom, a halogen atom (Cl, Br, I, F), a hydroxyl group, a cyano group, a nitro group, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_1$-$C_6$)-alkyl group, an amino-($C_1$-$C_{12}$)-alkyl group, or a carbocyclic or heterocyclic aromatic compound, a carboxamide or a sulfonamide;

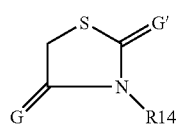
(VIII)

wherein G and G' can be equal or different and independently of each other denote an oxygen atom, a sulfur atom or an NR" amino group, with R" standing for hydrogen or a substituted or unsubstituted ($C_1$-$C_{12}$)-alkyl group, and R14 denotes hydrogen, a substituted or unsubstituted ($C_1$-$C_{12}$)-alkyl group or a carbocyclic or heterocyclic, substituted or unsubstituted aromatic compound;

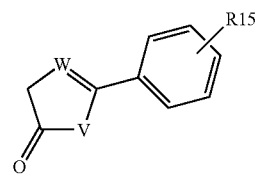
(IX)

wherein V stands for an oxygen atom or an NR'" amino group, with R'" denoting hydrogen, or a substituted or unsubstituted ($C_1$-$C_{,12}$)-alkyl group, and R15 stands for a hydrogen atom, a halogen atom, a hydroxyl group, a cyano, a nitro group, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_1$-C6)-alkyl group, an amino-($C_1$-$C_{12}$)-alkyl group, a carbocyclic or heterocyclic aromatic compound, a carboxamide or a sulfonamide;

and (c) at least one oxidant.

Depending on the pH of the agent, the compound of formula (I) can also be in equilibrium with the compound of formula (Ia):

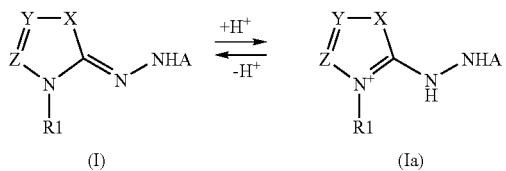

(I)            (Ia)

Preferred hydrazones are hydrazone derivatives of formula (I) or the physiologically compatible salts thereof wherein:
(i) X denotes a sulfur atom, Y denotes C—R3, Z denotes C—R4 and A stands for a hydrogen atom, or
(ii) X denotes N—R2, Y denotes nitrogen and A stands for a hydrogen atom;

the hydrazone derivatives of formula (I) or the physiologically compatible salts thereof wherein X denotes sulfur, Y denotes C—R3, Z denotes C—R4 and A stands for hydrogen being particularly preferred.

Examples of compounds of formula (I) are the following as well as the salts thereof:
3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H)-thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone, 4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)-thiazolone hydrazone,
4-[(1,1'-biphenyl)-4-yl]-3-methyl-2(3H)-thiazolone hydrazone,
3-methyl-4-(2-naphthalenyl)-2(3H)-thiazolone hydrazone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
4,5-diphenyl-3-methyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazono-2,3-dihydro-3-methyl-5-thiazole carbonitrile
4,5-dimethyl-3-ethyl-2(3H)-thiazolone hydrazone,
ethyl 2-hydrazono-2,3-dihydro-3-ethyl-4-methylthiazolecarboxylate,
5-methyl-3-(1-methylethyl)-4-phenyl-2(3H)-thiazolone hydrazone,
3-(1-methylethyl)-4,5-diphenyl-2(3H)-thiazolone hydrazone,
4,5-diphenyl-3-propyl-2(3H)-thiazolone hydrazone,
3-butyl-4,5-diphenyl-2(3H)-thiazolone hydrazone,
4,5-diphenyl-3-(2-methylpropyl)-2(3H)-thiazolone hydrazone,
3-hydroxyethyl-2(3H)-thiazolone hydrazone,
3-hydroxyethyl-4-methyl-2(3H)-thiazolone hydrazone,
3-aminoethyl-2(3H)-thiazolone hydrazone,
3-aminoethyl-4-methyl-2(3H)-thiazolone hydrazone,
3,4-diphenyl-2(3H)-thiazolone hydrazone,
4-methyl-3-phenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
3,4-diphenyl-5-methyl-2(3H)-thiazolone hydrazone,
3,4,5-triphenyl-2(3H)-thiazolone hydrazone,
4,5-dimethyl-3-(phenylmethyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-diphenyl-3-(2-propenyl)-2(3H)-thiazolone hydrazone,
ethyl 2-hydrazono-2,3-dihydro-3-[(phenylamino)carbonyl]-4-methylthiazolecarboxylate
3-methyl-4,5,6,7-tetrahydro-2(3H)-benzothiazolone hydrazone,
3-methyl-2(3H)benzothiazolone hydrazone,
3,6-dimethyl-2(3H)benzothiazolone hydrazone,
6-chloro-3-methyl-2(3H)benzothiazolone hydrazone,
7-chloro-3-methyl-2(3H)benzothiazolone hydrazone,
6-hydroxy-3-methyl-2(3H)benzothiazolone hydrazone,
5-methoxy-3-methyl-2(3H)benzothiazolone hydrazone,
7-methoxy-3-methyl-2(3H)benzothiazolone hydrazone,
5,6-dimethoxy-3-methyl-2(3H)benzothiazolone hydrazone,
5-ethoxy-3-methyl-2(3H)benzothiazolone hydrazone,
6-ethoxy-3-methyl-2(3H)benzothiazolone hydrazone,
3-methyl-5-nitro-2(3H)benzothiazolone hydrazone,
3-methyl-6-nitro-2(3H)benzothiazolone hydrazone,
5-acetamido-3-methyl-2(3H)benzothiazolone hydrazone,
6-acetamido-3-methyl-2(3H)benzothiazolone hydrazone,
5-anilino-3-methyl-2(3H)benzothiazolone hydrazone,
6-anilino-3-methyl-2(3H)benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,
[(2-hydrazono-2,3-dihydro-3-methyl-6-benzothiazolyl)oxy]acetic acid hydrazide,
(3-methylnaphtho[2,3-d]thiazole-2(3H)one hydrazone,
3-ethyl-2(3H)benzothiazolone hydrazone,
6-ethoxy-3-ethyl-2(3H)benzothiazolone hydrazone,
3-propyl-2(3H)benzothiazolone hydrazone,
3-butyl-2(3H)benzothiazolone hydrazone,
3-hexyl-2(3H)benzothiazolone hydrazone,
3-hydroxyethyl-2(3H)benzothiazolone hydrazone,
3-aminoethyl-2(3H)benzothiazolone hydrazone,
3-p-methylbenzyl-2(3H)benzothiazolone hydrazone,
2-hydrazono-2,3-dihydro-3-(2-hydroxyethyl)-6-benzothiazolecarboxylic acid,
2-hydrazono-2,3-dihydro-6-methoxy-3(2H)benzothiazolepropanesulfonic acid,
6-hexadecyloxy-2-hydrazono-3(2H)benzothiazolepropanesulfonic acid,
ethyl 2-keto-3-benzothiazoline acetate hydrazone,
3-acetyl-2(3H)-benzothiazolone hydrazone,
2-hydrazono-3(2H)benzothiazole carboxaldehyde,
3-methyl-2(3H)oxazolone hydrazone,
3-phenyl-2(3H)oxazolone hydrazone,
3-methyl-2(3H)benzoxazolone hydrazone,
3-phenyl-2(3H)benzoxazolone hydrazone,
1,3-dimethyl-4-imidazolin-2-one hydrazone,
1,3-diethyl-4-imidazolin-2-one hydrazone,
1,3-dihydroxyethyl-4-imidazolin-2-one hydrazone,
1,3-diaminoethyl-4-imidazolin-2-one hydrazone,
1,3-dimethyl-4-methoxy-4-imidazolin-2-one hydrazone,
1,3,4-trimethyl-4-imidazolin-2-one hydrazone,
1,3-dimethyl-4-phenyl-4-imidazolin-2-one hydrazone,
4-carboxy-1,3-dimethyl-4-imidazolin-2-one hydrazone,
4-amino-1,3-dimethyl-4-imidazolin-2-one hydrazone,
1,3-dimethyl-4-dimethylamino-4-imidazolin-2-one hydrazone,
1,3-dimethyl-2-benzimidazolinone hydrazone,
1,3-diethyl-2-benzimidazolinone hydrazone,
1,3-dihydroxyethyl-2-benzimidazolinone hydrazone,
1,3-diaminoethyl-2-benzimidazolinone hydrazone,
1,3,5-trimethyl-2-benzimidazolinone hydrazone,
5-methoxy-1,3-dimethyl-2-benzimidazolinone hydrazone,
5-bromo-1,3-dimethyl-2-benzimidazolinone hydrazone,
4,6-dibromo-1,3-dimethyl-2-benzimidazolinone hydrazone,
5-chloro-1,3-dimethyl-2-benzimidazolinone hydrazone,
1,3-dimethyl-5-nitro-2-benzimidazolinone hydrazone,
1,3-dimethyl-6-nitro-2-benzimidazolinone hydrazone,
1,4-dimethyl-Δ2-1,2,4-triazoline-5-one hydrazone, 1,4-dihydroxyethyl-Δ2-1,2,4-triazoline-5-one hydrazone,
1,4-diaminoethyl-Δ2-1,2,4-triazoline-5-one hydrazone,
1,3,4-trimethyl-Δ2-1,2,4-triazoline-5-one hydrazone,
1,4-dimethyl-3-phenyl-Δ2-1,2,4-triazoline-5-one hydrazone,
1,4-dimethyl-3-methoxy-Δ2-1,2,4-triazoline-5-one hydrazone,
1,4-dimethyl-3-dimethylamino-Δ2-1,2,4-triazoline-5-one hydrazone,
4-carboxy--1,4-dimethyl-Δ2-1,2,4-triazoline-5-one hydrazone,
4-amino-1,4-dimethyl-Δ2-1,2,4-triazoline-5-one hydrazone,
4-butyl-1-methyl-3-phenyl-Δ2-1,3,4-triazoline-5-one hydrazone,
4-methyl-Δ2-1,3,4-thiadiazoline-5-one hydrazone,
4-hydroxyethyl-Δ2-1,3,4-thiadiazoline-5-one hydrazone,
4-aminoethyl-Δ2-1,3,4-thiadiazoline-5-one hydrazone,
4-methyl-2-phenyl-Δ2-1,3,4-thiadiazoline-5-one hydrazone,
2-methoxy-4-methyl-Δ2-1,3,4-thiadiazoline-5-one hydrazone,
2-anilino-4-methyl-Δ2-1,3,4-thiadiazoline-5-one hydrazone,
2-amino-4-methyl-Δ2-1,3,4-thiadiazoline-5-one hydrazone,
2-dimethylamino-4-methyl-Δ2-1,3,4-thiadiazoline-5-one hydrazone,
4-methyl-2-(methylthio)-Δ2-1,3,4-thiadiazoline-5-one hydrazone,
4-(5-hydrazono-4,5-dihydro-4-methyl-1,3,4-thiadiazol-2-yl)benzenesulfonyl fluoride,
4-methyl-Δ2-1,2,4-thiadiazoline-5-one hydrazone,
4-hydroxyethyl-Δ2-1,2,4-thiadiazoline-5-one hydrazone,
4-aminoethyl-Δ2-1,2,4-thiadiazoline-5-one hydrazone,
4-methyl-3-phenyl-Δ2-1,2,4-thiadiazoline-5-one hydrazone,
3-methoxy-4-methyl-Δ2-1,2,4-thiadiazoline-5-one hydrazone,
3-amino-4-methyl-Δ2-1,2,4-thiadiazoline-5-one hydrazone,
3-dimethylamino-4-methyl-Δ2-1,2,4-thiadiazoline-5-one hydrazone,
3-carboxy-4-methyl-Δ2-1,2,4-thiadiazoline-5-one hydrazone,
1,4-dimethyl-Δ2-1,2,4-triazoline-5-one hydrazone,
1,4-dihydroxyethyl-Δ2-1,2,4-triazoline-5-one hydrazone,
1,4-diaminoethyl-Δ2-1,2,4-triazoline-5-one hydrazone,
1,3,4-trimethyl-Δ2-1,2,4-triazoline-5-one hydrazone,
1,4-dimethyl-3-phenyl-Δ2-1,2,4-triazoline-5-one hydrazone and
4-methyl-3-phenyl-Δ2-1,2,4-triazoline-5-one hydrazone.

Among the compounds of formula (I), the following thiazolone hydrazone derivatives and the salts thereof are particularly preferred:
3-methyl-2(3H)thiazolone hydrazone,
3,4-dimethyl-2(3H)thiazolone hydrazone,
4-tert.butyl-3-methyl-2(3H)thiazolone hydrazone,
3-methyl-4-phenyl-2(3H)thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)thiazolone hydrazone,
4-[(1,1'-biphenyl)-4-yl]-3-methyl-2(3H)-thiazolone hydrazone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
4,5-diphenyl-3-methyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazino-2,3-dihydro-3-methyl-5-thiazole carbonitrile
4,5-dimethyl-3-ethyl-2(3H)-thiazolone hydrazone,
ethyl 2-hydrazono-2,3-dihydro-3-ethyl-4-methylthiazole-carboxylate,
5-methyl-3-(1-methylethyl)-4-phenyl-2(3H)-thiazolone hydrazone,
4,5-diphenyl-3-(1-methylethyl)-2(3H)-thiazolone hydrazone
4,5-diphenyl-3-propyl-2(3H)-thiazolone hydrazone,
3-butyl-4,5-diphenyl-2(3H)-thiazolone hydrazone,
4,5-diphenyl-3-(2-methylpropyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-diphenyl-3-(2-propenyl)-2(3H)-thiazolone hydrazone,
3-hydroxyethyl-2(3H)-thiazolone hydrazone,
3-hydroxyethyl-4-methyl-2(3H)-thiazolone hydrazone,
3-aminoethyl-2(3H)-thiazolone hydrazone,
3-aminoethyl-4-methyl-2(3H)-thiazolone hydrazone,
3-phenyl-2(3H)-thiazolone hydrazone,
4-methyl-3-phenyl-2(3H)-thiazolone hydrazone,
3,4-diphenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
3,4-diphenyl-5-methyl-2(3H)-thiazolone hydrazone,
3,4,5-triphenyl-2(3H)-thiazolone hydrazone,
4,5-dimethyl-3-(phenylmethyl)-2(3H)-thiazolone hydrazone,
ethyl 2-hydrazono-2,3-dihydro-3-[(phenylamino)carbonyl]-4-methylthiazolecarboxylate 3-methyl-4,5,6,7-tetrahydro-2(3H)-benzothiazolone hydrazone,
3-methyl-2(3H)benzothiazolone hydrazone,
3,6-dimethyl-2(3H)benzothiazolone hydrazone,
6-chloro-3-methyl-2(3H)benzothiazolone hydrazone,
7-chloro-3-methyl-2(3H)benzothiazolone hydrazone,
6-hydroxy-3-methyl-2(3H)benzothiazolone hydrazone,
5-methoxy-3-methyl-2(3H)benzothiazolone hydrazone,
7-methoxy-3-methyl-2(3H)benzothiazolone hydrazone,
5,6-dimethoxy-3-methyl-2(3H)benzothiazolone hydrazone,
5-ethoxy-3-methyl-2(3H)benzothiazolone hydrazone,
6-ethoxy-3-methyl-2(3H)benzothiazolone hydrazone,
3-methyl-5-nitro-2(3H)benzothiazolone hydrazone,
3-methyl-6-nitro-2(3H)benzothiazolone hydrazone,
5-acetamido-3-methyl-2(3H)benzothiazolone hydrazone,
6-acetamido-3-methyl-2(3H)benzothiazolone hydrazone,
5-anilino-3-methyl-2(3H)benzothiazolone hydrazone,
6-anilino-3-methyl-2(3H)benzothiazolone hydrazone, 2-hydrazono-2,3-dihydro-3-methyl-6-benzothiazolecarboxylic acid, 2-hydrazono-2,3-dihydro-3-methyl-4-benzothiazolesulfonic acid, 2-hydrazono-2,3-dihydro-3-methyl-5-benzothiazolesulfonic acid, 2-hydrazono-2,3-dihydro-3-methyl-6-benzothiazolesulfonic acid, 2-hydrazono-2,3-dihydro-3-methyl-7-benzothiazolesulfonic acid, 2-hydrazono-2,3-dihydro-N,N,3-trimethyl-6-benzothiazolesulfonamide,

[(2-hydrazono-2,3-dihydro-3-methyl-6-benzothiazolyl)oxy] acetic acid hydrazide, 3-methylnaphtho[2,3-d]thiazol-2(3H)one hydrazone 3-ethyl-2(3H)benzothiazolone hydrazone, 6-ethoxy-3-ethyl-2(3H)benzothiazolone hydrazone, 3-propyl-2(3H)benzothiazolone hydrazone, 3-butyl-2(3H)benzothiazolone hydrazone, 3-hexyl-2(3H)benzothiazolone hydrazone, 3-hydroxyethyl-2(3H)benzothiazolone hydrazone, 3-aminoethyl-2(3H)benzothiazolone hydrazone, 3-p-methylbenzyl-2(3H)benzothiazolone hydrazone, 2,3-dihydro-2-hydrazono-3-(2-hydroxyethyl)-6-benzothiazolecarboxylic acid 2,3-dihydro-2-hydrazono-6-methoxy-3(2H)benzothiazolepropanesulfonic acid, 6-hexadecyloxy-2-hydrazono-3(2H)benzothiazolepropanesulfonic acid, ethyl 2-keto-3-benzothiazolineacetate hydrazone, 3-acetyl-2(3H)benzothiazolone hydrazone and 2-hydrazono-3(2H)benzothiazole carboxaldehyde.

Some compounds of formula (I) are commercially available, but they can also be prepared by me-thods of synthesis known from the literature, for example by the method described in Research Disclosure 174, pp. 42-44 (1978) or in analogy with the method described in DE-A 1 049 381.

Suitable CH-active compounds of general formulas (II) to (IX) are, in particular, the following compounds and the salts thereof:

cyanoacetic acid, methyl cyanoacetate, ethyl cyanoacetate, malonic acid dinitrile, pivaloylaceto-nitrile, 2-cyanoacetamide, 2-cyano-1-methyl-4-nitrobenzene, barbituric acid, thiobarbituric acid, 1,3-dimethylthiobarbituric acid, 1-methyl-1,2-dihydro-6-hydroxy-4-methyl-2-ketopyridine-3-carbonitrile, 1-ethyl-1,2-dihydro-6-hydroxy-4-methyl-2-ketopyridine-3-carbonitrile, 1-hydroxyethyl-1,2-dihydro-6-hydroxy-4-methyl-2-ketopyridine-3-carbonitrile, 1,3-dihydro-2H-indol-2-one, benzofuran-3(2H)-one, 2-phenyl-3,5-dihydroimidazol-4-one, 3-indoxyl acetate, 2-thioxo-4-thiazolidinone and 4-keto-2-thioxo-3-thiazolidinylacetic acid, among which the following compounds are particularly preferred: cyanoacetic acid, methyl cyanoacetate, ethyl cyanoacetate, malonicacid dinitrile, barbituric acid, thiobarbituric acid, 1,3-dimethylthiobarbituric acid, 1,3-dihydro-2H-indol-2-one, 2-thioxo-4-thiazolidinone and 4-keto-2-thioxo-3-thiazoldinylacetic acid.

The colorants of the invention are used in conjunction with an oxidant. Suitable oxidants are those usually employed in hair colorants, for example hydrogen peroxide or the addition com-pounds thereof, persalts such as the persulfate salts and perborate salts, or peracids and enzymatic oxidation systems. Air oxidation is also feasible. Preferred oxidants are hydrogen peroxide or the addition compounds thereof (for example sodium percarbonate, urea peroxide etc) and the persalts such as the persulfate salts or perborate salts, for example potassium persulfate, sodium persulfate or ammonium persulfate, as well as mixtures thereof.

The oxidants are contained in the ready-to-use colorant (A) in a total amount from about 0.01 to 10 weight percent and preferably from about 0.1 to 5 weight percent.

Moreover, besides the compounds of formula (I) and compounds of formulas (II) to (IX), the colorant of the invention can also contain other common, physiologically unobjectionable direct dyes from the group of cationic and anionic dyes, disperse dyes, azo dyes, quinone dyes and triphenylmethane dyes. The direct dyes are contained in the ready-to-use colorant (A) in an amount from about 0.01 to 10 weight percent and preferably from about 0.1 to 5 weight percent.

Each of the compounds of formula (I) and of the compounds of formulas (II) to (IX) is contained in the ready-to-use colorant (A) in a total amount from about 0.01 to weight percent and preferably from about 0.1 to 5 weight percent.

As a rule, the compounds of formula (I) and the compounds of formulas (II) to (IX) are stored separately from one another and are mixed with the oxidant only just before use. It is also possible, however, provided the compounds of formula (I), the compounds of formulas (II) to (IX) and the oxidant are solids, to package them together and to obtain the ready-to-use colorant (A) just before use by mixing the compounds of formula (I), the compounds of formulas (II) to (IX) and the oxidant with water or with a liquid preparation containing the other components of the colorant. It is also possible, provided the compounds of formula (I) and the compounds of formulas (II) to (IX) are solids, to package them together and to prepare the ready-to-use colorant (A) by mixing the compounds of formula (I) and the compounds of formulas (II) to (IX) with the oxidant just be-fore use.

The colorant of the invention thus as a rule consists of several components that are mixed with one another just before use. Preferably, the colorant is provided as a 2-component kit consisting of dye carrier com-position (A1) containing the compounds of formula (I) and an additional dye carrier composition (A2) containing the compounds of formulas (II) to (IX) and optionally an oxidant, or it is provided as a 3-component kit consisting of a dye carrier composition (A1) containing the compounds of formula (I), another dye carrier composition (A2) containing the com-pounds of formulas (II) to (IX) and a third component (A3) containing an oxidant.

Particularly preferred is a 3-component kit consisting of a dye carrier composition (A1) containing the compounds of formula (I), another dye carrier composition (A2) containing the compounds of formulas (II) to (IX) and a third component (A3) containing an oxidant.

Another object of the present invention is a multicomponent kit consisting of a preparation of component (A1) and a preparation of component (A2), the oxidant possibly being packaged as component (A3) separately from component (A2), and optionally of an agent for adjusting the pH (an alkalinizing agent or an acid). Naturally, the preparations of components (A1) and (A2) can consist of several individual components that are mixed with one another just before use. Another possibility is a 2-component kit of which the 1st component consists of a powder containing the compounds of formula (I), the compounds of formulas (II) to (IX) and optionally an oxidant, provided the compounds of formula (I), the compounds of formulas (II) to (IX) and the oxidant are solids, and optionally other common powdered cosmetic additives, and the 2nd component of which is water or a liquid cosmetic preparation. Preferred is a 2-component kit of which the 1st component consists of a powder containing the compounds of formula (I), the compounds of formulas (II) to (IX) and the oxidant and optionally other common powdered cosmetic additives, and the 2nd component of which is water or a liquid cosmetic preparation.

The components (A1) and (A2) and ready-to-use colorant (A) are provided, for example, as a solution, particularly an aqueous or aqueous-alcoholic solution, a cream, a gel or an emulsion. Their composition consists of a mixture of the compound of formula (I) or compound of formulas (II) to (IX) and optionally of an oxidant, with the additives normally used for such preparations.

Commonly used additives to solutions, creams, emulsions, gels or aerosol foams are, for ex-ample, solvents such as water, the lower aliphatic alcohols, for example ethanol, n-propanol and isopropanol, or glycols such as glycerol and 1,2-propanediol, furthermore wetting agents or emulsifiers from the classes of anionic, cationic, amphoteric or nonionic surface-active substan-ces, such as the fatty alcohol sulfates, ethoxylated fatty alcohol sulfates, alkyl sulfonates, alkyl benzenesulfonates, alkyltrimethylammonium salts, alkylbetaines, ethoxylated fatty alcohols, eth-oxylated nonylphenols, fatty alkanolamides, ethoxylated fatty esters, furthermore thickeners such as the higher fatty alcohols, starch or cellulose derivatives, perfumes, hair pretreatment agents, conditioners, hair-swelling agents, preservatives, furthermore vaselines, paraffin oil and fatty acids and also hair-care agents such as cationic resins, lanolin derivatives, cholesterol, pantothenic acid and betaine. The said constituents are used in amounts usually employed for such purposes, for example the wetting agents and emulsifiers at a concentration of about 0.5 to 30 weight percent [in all cases based on component (A1) or (A2)], the thickeners in an amount of about 0.1 to 25 weight percent [in all cases based on component (A1) or (A2)] and the hair-care agents at a concentration of about 0.1 to 5.0 weight percent [in all cases based on component (A1) or (A2)].

The pH of the ready-to-use colorant (A) is in all cases about 6 to 12 and preferably about 7 to 11. The ready-to-use colorant (A) is adjusted to the pH desired for the coloring by addition of an alkalinizing agent, for example ammonia, an amino acid, alkanolamine, alkali metal hydroxide, alkaline earth metal hydroxide, alkali metal acetate, alkaline earth metal acetate, ammonium carbonate, alkali metal carbonate, alkaline earth metal carbonate, alkali metal silicate, alkaline earth metal silicate or ammonium silicate, or by addition of an acid, for example lactic acid, acetic acid, tartaric acid, phosphoric acid, hydrochloric acid, citric acid, ascorbic acid or boric acid.

The ready-to-use colorant is prepared just before use by mixing components (A1) and (A2) or (A1), (A2) and (A3), optionally with addition of an alkalinizing agent or an acid, and is then applied to the fibers, particularly human hair. Depending on the color depth desired, this mixture is allow-ed to act for about 5 to 60 minutes, preferably about 15 to 30 minutes, at a temperature of about 20 to 50° C. and particularly about 30 to 40° C. The fibers are then rinsed with water, optionally washed with a shampoo and dried.

The colorant of the invention imparts to the fibers, particularly keratin fibers, for example human hair, a uniform, intense, brilliant and lasting coloration.

The following examples will provide a more detailed explanation of the subject matter without limiting it to these examples.

EXAMPLES

Example 1

Synthesis of 3,4-dimethyl-2(3H)thiazolone hydrazone hydrochloride

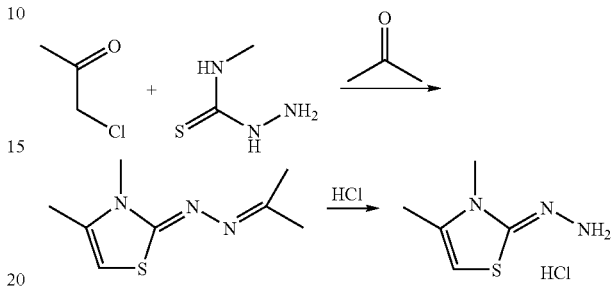

Step A: 3.4-Dimethyl-2(3H)thiazolone-(1-methylethylidene) hydrazone 21 g (200 mmol) of 4-methyl-3-thiosemicarbazide in 1000 mL of acetone was heated at reflux for 2 hours. To this solution was then added dropwise 20.4 g (220 mmol) of chloroacetone. The reaction mixture was allowed to reflux for 7 hours and was then concentrated. The resulting crude product was recrystallized from acetone. This gave 23 g of an orange-colored powder (63% of the theoretical).

Melting Point: 139-139.6° C.

$^1$H—NMR (DMSO, 300 MHz): δ=6.72 [s, broad, 1H, H—C(5)]; δ=3.67 (s, 3H, N—CH$_3$); δ=2.27 [d, J=0.9 Hz, 3H, CH$_3$—C(4)]; δ=2.17 (s, 3H, CH$_3$); δ=2.07 (s, 3H, CH$_3$)

$^{13}$C—NMR (DMSO, 300 MHz): δ=169.16; 164.14; 139.02 [C(4)]; 103.36 [C(5)]; 34.47 (CH$_3$N); 24.60; 19.91; 13.53 [CH$_3$(C4)].

MS (ESI): 184 (M$^+$+1)

Step B: 3.4-Dimethyl-2(3H)thiazolone hydrazone hydrochloride 3.5 g (19 mmol) of 3,4-dimethyl-2(3H)thiazolone-(1-methylethylidene) hydrazone from step A in 60 mL of 6 M hydrochloric acid was heated at 50° C. for 30 minutes. The reaction mixture was then concentrated, and the crude product was recrystallized from ethanol. This gave 2 g (60% of the theoretical) of a pink-colored powder.

Melting Point: 156.4-156.6° C.

$^1$H—NMR (DMSO, 300 MHz): δ=6.58 [q, J=0.9 Hz, 1H, H—C(5)]; δ=3.41 (s, 3H, N—CH$_3$); δ=2.18 [d, 0.9 Hz, 3H, CH$_3$—C(4)].

MS (ESI): 144 (M$^+$+1).

$^{13}$C—NMR (DMSO, 300 MHz): δ=172.30 [C(2)]; 138.79 [C(4)]; 101.43 [C(5)]; 32.92 (CH$_3$N); 13.40 [CH$_3$(C4)];

CHN Analysis: [C$_5$H$_9$N$_3$S (0.96 HCl)(0.5 EtOH)]:

| | % C | % H | % N | % S | % Cl |
|---|---|---|---|---|---|
| Calculated: | 35.81 | 6.49 | 20.88 | 15.93 | 16.90 |
| Found: | 35.20 | 6.30 | 21.00 | 15.40 | 16.80 |

Examples 2-6

Colorants with 3,4-dimethyl-2(3H)thiazolone hydrazone hydrochloride

Component (A1)

| | |
|---|---|
| 4.00 g | of decylpolyglucose, 50% aqueous solution |
| 0.20 g | of disodium ethylenediaminetetraacetate hydrate |
| 5.00 g | of ethanol |
| 0.45 g | of 3,4-dimethyl-2(3H)thiazolone hydrazone hydrochloride |
| to 100.00 g | water, demineralized |

Component (A2)

| | |
|---|---|
| Y g | of CH-active compound as per Table 1 |
| 0.40 g | of potassium persulfate |

The foregoing constituents were mixed uniformly with one another at room temperature (20-25° C.) or with slight heating (35-40° C.). The pH of the ready-to-use colorant (A) was adjusted to the value given in Table 1 with sodium hydroxide solution, sodium carbonate or ammonia.

The ready-to-use colorant was applied to bleached hair and uniformly distributed with a brush. After an exposure time of 30 min at 40° C., the hair was rinsed with lukewarm water, washed with a commercial shampoo, rinsed with lukewarm water and then dried.

The amount of CH-active compound of formulas (II) to (IX) used and the resulting colorations are collected in the following Table 1.

TABLE 1

| Example No. | CH-Active Compound Used, (Amount in g) | | pH | Coloration |
|---|---|---|---|---|
| 2 | thiobarbituric acid | (0.36 g) | 9.3 | yellow |
| 3 | 1,3-dihydro-2H-indol-2-one | (0.33 g) | 9.8 | yellow |
| 4 | 2-thioxo-4-thiazolidinone | (0.33 g) | 9.2 | orange |
| 5 | ethyl cyanoacetate | (0.28 g) | 9.7 | yellow-green |
| 6 | malonic acid dinitrile | (0.17 g) | 9.1 | golden-yellow |

Examples 7+8

Colorants with 3-Methyl-2(3H)-benzothiazolone hydrazone hydrochloride

Component (A1)

| | |
|---|---|
| 4.00 g | of decylpolyglucose, 50% aqueous solution |
| 0.20 g | of disodium ethylenediaminetetraacetate hydrate |
| 5.00 g | of ethanol |
| 0.58 g | of 3-methyl-2(3H)-benzothiazolone hydrazone hydrochloride hydrate |
| to 100.00 g | demineralized water |

Component (A2)

| | |
|---|---|
| Y g | of CH-active compound as per Table 2 |
| 0.40 g | of potassium persulfate |

The afore-indicated components were mixed with one another homogeneously at room temperature (20-25° C.) or with gentle heating (35-40° C.). If necessary, the pH of the ready-to-use colorant (A) was adjusted to the value given in Table 2 with sodium hydroxide solution, sodium carbonate, ammonia or citric acid.

The ready-to-use colorant was applied to bleached hair and uniformly distributed with a brush. After an exposure time of 30 minutes at 40° C., the hair was rinsed with lukewarm water, washed with commercial shampoo, rinsed with lukewrm water and then dried.

The amount of CH-active compound of formulas (II) to (IX) and the colorations obtained are collected in the following Table 2.

TABLE 2

| Example No. | CH-Active Compound Used, (Amount in g) | pH | Coloration |
|---|---|---|---|
| 7 | thiobarbituric acid    (0.36 g) | 9.3 | copper shades |
| 8 | malonic acid dinitrile (0.17 g) | 9.1 | golden-yellow |

Unless otherwise indicated, all percentages given in the present application are by weight.

The invention claimed is:

1. A ready-to-use agent for coloring keratin fibers, wherein said ready-to-use agent contains
  (a) at least one hydrazone derivative of formula (I), or a physiologically compatible salt thereof:

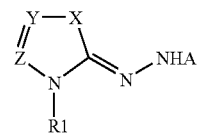

(I)

wherein X denotes oxygen, sulfur or N—R2,
  Y denotes C—R3 or nitrogen, and
  Z denotes C—R4 or nitrogen,
  provided that a heterocyclic ring in said at least one hydrazone derivative of the formula (I) contains at the most three hetero atoms;
  A denotes hydrogen, an acetyl group, a trifluoroacetyl group, a formyl group, a $(C_1-C_6)$-alkyl-sulfonyl group, or an arylsulfonyl group;
  R1 and R2 are the same or different and, independently of each other, denote a saturated or unsaturated $(C_1-C_{12})$-alkyl group, a halogen-substituted $(C_1-C_{12})$-alkyl group, a hydroxy-$(C_1-C_{12})$-alkyl group, an amino-$(C_1-C_{12})$-alkyl group, a sulfonic acid-$(C_1-C_{12})$-alkyl group, a formyl group, a —C(O)—$(C_1-C_{12})$-alkyl group, a substituted or unsubstituted —C(O)-phenyl group, a —C(O)NH—$(C_1-C_{12})$-alkyl group, a substituted or unsubstituted —C(O)NH-phenyl group, a substituted or unsubstituted phenyl group, or a benzyl group;
  R3 and R4 are the same or different and, independently of each other, denote hydrogen, a halogen atom, a saturated or unsaturated $(C_1-C_{12})$-alkyl group, a halogen-substituted $(C_1-C_{12})$-alkyl group, a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a di$(C_1-C_{12})$-alkylamino group, a carboxyl group, a —C(O)O—$(C_1-C_{12})$-alkyl group, a substituted or unsubstituted —C(O)O-phenyl group, a substituted or unsubstituted phenyl group, or a naphthyl group;

and when Y and Z denote C—R3 and C—R4, R3 and R4 together with a remainder of the hydrazone derivative can form a heterocyclic or carbocyclic, saturated or unsaturated, substituted or unsubstituted ring system;

(b) at least one CH-active compound selected from the group consisting of compounds of formulas (II) to (IX) as follows:

(II)

wherein R5 denotes a cyano group, a (CO)—R6 carbonyl group, wherein R6 denotes a $(C_1-C_{12})$-alkoxy group, an amino group, a $(C_1-C_{12})$-alkylamino group, a $(C_1-C_{12})$-alkyl group or an aryl group;

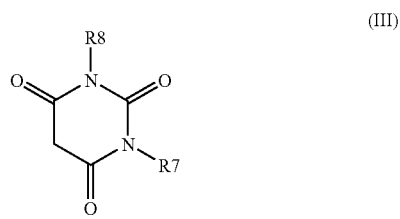

(III)

wherein R7 and R8 are the same or different and, independently of each other, denote hydrogen, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1C_6)$-alkoxy-$(C_2-C_6)$-alkyl group, an amino-$(C_1-C_{12})$-alkyl group, or a carbocyclic or heterocyclic, substituted or unsubstituted aromatic compound, and D denotes a sulfur atom or an oxygen atom;

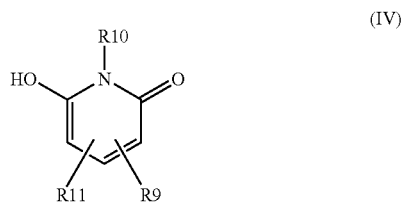

(IV)

wherein R9 denotes a hydrogen atom, a nitrile group, a $(C_1-C_{12})$-alkyl group, a carbocyclic or heterocyclic aromatic compound or a (CO)—R12 carbonyl group, wherein R12 denotes hydrogen, a hydroxyl group, a $(C_1-C_{12})$-alkoxy group, an amino group, a $(C_1-C_{12})$-alkylamino group, a $(C_1-C_{12})$-alkyl group, or an aryl group; and R10 and R11 are the same or different and, independently or each other, denote hydrogen, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_2-C_6)$-alkyl group, an amino-$(C_1-C_{12})$-alkyl group, or a carbocyclic or heterocyclic aromatic compound;

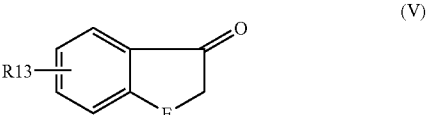

(V)

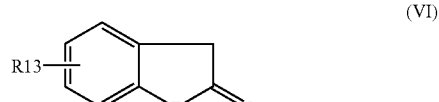

(VI)

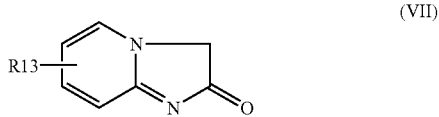

(VII)

wherein E denotes an oxygen atom, a sulfur atom of an NR' amino group, with R' denoting hydrogen or a substituted or unsubstituted $(C_1-C_{12})$-alkyl group, and R13 denotes a hydrogen atom, a halogen atom, a hydroxyl group, a cyano group, a nitro group, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_1-C_6)$-alkyl group, an amino-$(C_1-C_{12})$-alkyl group, a carbocyclic or heterocyclic aromatic group, a carboxamide group, or a sulfonamide group;

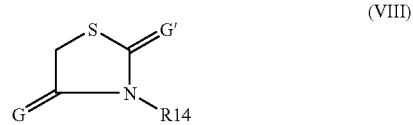

(VIII)

wherein G and G' are the same or different and, independently or each other, denote an oxygen atom, a sulfur atom, or an NR" amino group, with R" denoting hydrogen or a substituted or unsubstituted $(C_1-C_{12})$-alkyl group, R14 denotes hydrogen, a substituted or unsubstituted $(C_1-C_{12})$-alkyl group or a carbocyclic or heterocyclic, substituted or unsubstituted aromatic compound; and

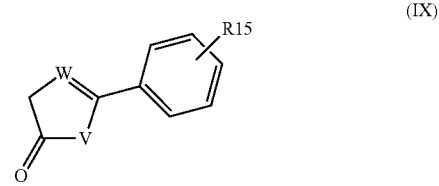

(IX)

wherein V denotes an oxygen atom or an NR''' amino group, with R''' denoting hydrogen or a substituted or unsubstituted-$(C_1-C_{12})$-alkyl group; and R15 denotes a hydrogen atom, a halogen atom, a hydroxyl group, a cyano group, a nitro group, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_1-C_6)$-alkyl group, an amino-$(C_1-C_{12})$-alkyl group, a carbocyclic or heterocyclic aromatic group, a carboxamide group, or a sulfonamide group;

and (c) at least one oxidant.

2. The agent as defined in claim 1, wherein X denotes sulfur, Y denotes C—R3, Z denotes C—R4 and A denotes hydrogen.

3. The agent as defined in claim 1, wherein said at least one hydrazone derivative of the formula (I) is selected from the group consisting of
3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H)-thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(3-nitrophenyl)-2(3H)thiazolone hydrazone,
3-methyl-4-(4-nitrophenyl)-2(3H)-thiazolone hydrazone,
4-[(1,1'-biphenyl)-4-yl]-3-methyl-2(3H)-thiazolone hydrazone.
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
4,5-diphenyl-3-methyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazoione hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazole-carboxylate,
4-amino-2-hydrazono-2,3-dihydro-3-methyl-5-thiazole carbonitrile
4,5-dimethyl-3-ethyl-2(3H)-thiazolone hydrazone,
ethyl 2-hydrazono-2,3-dihydro-3-ethyl-4-methylthiazole-carboxylate,
5-methyl-3-(1-methylethyl)-4-phenyl-2(3H)-thiazolone hydrazone,
4,5-diphenyl-3-(1-methylethyl)-2(3H)-thiazolone hydrazone
4,5-diphenyl-3-propyl-2(3H)-thiazolone hydrazone,
3-butyl-4,5-diphenyl-2(3H)-thiazolone hydrazone,
4,5-diphenyl-3-(2-methylpropyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-diphenyl-3-(2-propenyl)-2(3H)-thiazolone hydrazone,
3-hydroxyethyl-2(3H)-thiazolone hydrazone,
3-hydroxyethyl-4-methyl-2(3H)-thjazolone hydrazone,
3-aminoethyl-2(3H)-thiazolone hydrazone,
3-aminoethyl-4-methyl-2(3H)-thiazolone hydrazone,
3-phenyl-2(3H)-thiazolone hydrazone,
4-methyl-3-phenyl-2(3H)-thiazolone hydrazone,
3,4-diphenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
3,4-diphenyl-5-methyl-2(3H)-thiazolone hydrazone, 3,4,5-triphenyl-2(3H)-thiazolone hydrazone,
4,5-dimethyl-3-(phenylmethyl)-2(3H)-thiazolone hydrazone,
ethyl 2-hydrazono-2,3-dihydro-3-[(phenylamino)carbonyl]-4-methylthiazolecarboxylate
3-methyl-4,5,6,7-tetrahydro-2(3H)-benzothiazolone hydrazone,
3-methyl-2(3H)-benzothiazolone hydrazone,
3,6-dimethyl-2(3H)-benzothiazolone hydrazone,
6-chloro-3-methyl-2(3H)-benzothiazolone hydrazone,
7-chloro-3-methyl-2(3H)-benzothiazolone hydrazone,
6-hydroxy-3-methyl-2(3H)-benzothiazolone hydrazone,
5-methoxy-3-methyl-2(3H)-benzothiazolone hydrazone,
7-methoxy-3-methyl-2(3H)-benzothiazolone hydrazone.
5,6-dimethoxy-3-methyl-2(3H)-benzothiazolone hydrazone,
5-ethoxy-3-methyl-2(3H)-benzothiazolone hydrazone,
6-ethoxy-3-methyl-2(3H)-benzothiazolone hydrazone,
3-methyl-5-nitro-2(3H)-benzothiazolone hydrazone,
3-methyl-6-nitro-2(3H)-benzothiazolone hydrazone,
5-acetamido-3-methyl-2(3H)-benzothiazolone hydrazone,
6-acetamido-3-methyl-2(3H)-benzothiazolone hydrazone,
6-anilino-3-methyl-2(3H)-benzothiazolone hydrazone,
6-anilino-3-methyl-2(3H)-benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,
[(2-hydrazono-2,3-dihydro-3-methyl-6-benzothiazolyl)oxy]acetic acid hydrazide,
3-methylnaphtho-[2,3-d]thiazol-2(3H)-one hydrazone
3-ethyl-2(3H)-benzothiazolone hydrazone,
6-ethoxy-3-ethyl-2(3H)-benzothiazolone hydrazone,
3-propyl-2(3H)-benzothiazolone hydrazone,
3-butyl-2(3H)-benzothiazolone hydrazone,
3-hexyl-2(3H)-benzothiazolone hydrazone,
3-hydroxyethyl-2(3H)-benzothiazolone hydrazone,
3-aminoethyl-2(3H)-benzothiazolone hydrazone,
3-p-methylbenzyl-2(3H)-benzothiazolone hydrazone,
2-hydrazono-2,3-dihydro-3-(2-hydroxyethyl)-6-benzothiazolecarboxylic acid
2-hydrazono-2,3-dihydro-6-methoxy-3(2H)-benzothiazole propane sulfonic acid,
6-hexadecyloxy-2-hydrazono-3(2H)-benzothiazole propane sulfonic acid, ethyl 2-keto-3-benzothiazolineacetate hydrazone, 3-acetyl-2(3H)benzothiazolone hydrazone and 2-hydrazono-3(2H)benzothiazole carboxaidehyde.

4. The agent as defined in claim 1, wherein said at least one active CH-active compound is selected from the group consisting of cyanoacetic acid, methyl cyanoacetate, ethyl cyanoacetate, malonic acid dinitrile, pivaloylacetonitrile,2-cyanoacetamide, 2-cyano-1-methyl-4-nitrobenzene, barbituric acid, thiobarbituric acid, 1,3-dimethylthiobarbituric acid, 1-methyl-1,2-dihydro-6-hydroxy-4-methyl-2-ketopyridine-3-carbonitrile, 1-ethyl-1,2-dihydro-6-hydroxy-4-methyl-2-ketopyridine-3-carbonitrile, 1-hydroxyethyl-1,2-dihydro-6-hydroxy-4-methyl-2-ketopyridine-3-carbonitrile, 1,3-dihydro-2H-indol-2-one, benzofuran-3(2H)-one, 2-phenyl-3,5-dihydroimidazol-4-one, 3-indoxyl acetate, 2-thioxo-4-thiazolidinone and 4-keto-2-thioxo-3-thiazolidinylacetic acid.

5. The agent as defined in claim 1, wherein said at least one oxidant is selected from the group consisting of hydrogen peroxide, addition compounds of said hydrogen peroxide, persalts, peracids and enzymatic oxidation systems.

6. The agent as defined in claim 1, wherein said at least one oxidant is selected from the group consisting of hydrogen peroxide, addition products of said hydrogen peroxide and persalts.

7. The agent as defined in claim 1, containing from 0.01 to 10 weight percent of said at least one hydrazone derivative of the formula (I), from 0.01 to 10 weight percent of said at least one CH-active compound, and from 0.01 to 10 weight percent of said at least one oxidant.

8. The agent as defined in claim 1, additionally containing from 0.01 to 10 weight percent of a physiologically unobjectionable direct dye and wherein said physiologically unobjectionable direct dye is selected from the group consisting of cationic dyes, anionic dyes, disperse dyes, nitro dyes, azo dyes, quinone dyes and triphenylmethane dyes.

9. The agent as defined in claim 1, having a pH from 7 to 11.

10. The agent as defined in claim 1, which is a hair colorant.

11. A two-component kit consisting of
a first dye carrier component (A1) comprisina at least one hydrazone derivative of formula (I), or a physiologically compatible salt thereof:

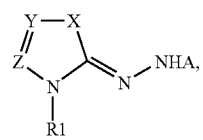
(I)

wherein X denotes oxygen, sulfur or N—R2,
Y denotes C—R3 or nitrogen, and
Z denotes C—R 4 or nitrogen,
provided that a heterocyclic ring in said at least one hydrazone derivative of the formula (I) contains at the most three hetero atoms;
A denotes hydrogen, an acetyl group, a trifluoroacetyl group, a formyl group, a ($C_1$-$C_6$)-alkyl-sulfonyl group, or an arylsulfonyl group;
R1 and R2 are the same or different and, independently of each other, denote a saturated or unsaturated ($C_1$-$C_{12}$)-alkyl group, a halogen-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a —C(O)O—$C_1$-$C_{12}$-alkyl group, a substituted or unsubstituted —C(O)O-phenyl group,a —C(O)NH—($C_1$-$C_{12}$)-alkyl group, a substituted or unsubstituted —C(O)NH-phenyl group, a substituted or unsubstituted phenyl group, or a benzyl group;
R3 and R4 are the same or different and, independently of each other, denote hydrogen, a halogen atom, a saturated or unsaturated ($C_1$-$C_{12}$)-alkyl group, a halogen-substituted ($C_1$-$C_{12}$)-alkyl group, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a di($C_1$-$C_{12}$)-alkylamino group, a carboxyl group, a —C(O)O—($C_1$-$C_{12}$)-alkyl group, a substituted or unsubstituted —C(O)O-phenyl group, a substituted or unsubstituted phenyl group, or a naphthyl group;
and when Y and Z denote C—R3 and C—R4, R3 and R4 together with a remainder of the hydrazone derivative can form a heterocyclic or carbocyclic, saturated or unsaturated, substituted or unsubstituted ring system; and
a second dye carrier component (A2) comprising an oxidant and at least one OH-active compound selected from the group consisting of compounds of formulas (II) to (IX) as follows:

(II)

wherein R5 denotes a cyano group, a (CO)—R6 carbonyl group, wherein R6 denotes a ($C_1$-$C_{12}$)-alkoxy group, an amino group, a ($C_1$-$C_{12}$)-alkylamino group, a ($C_1$-$C_{12}$)-alkyl group or an aryl group;

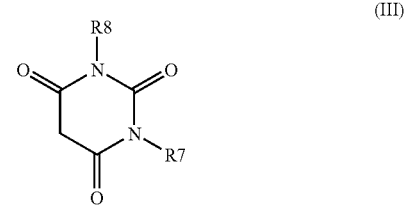
(III)

wherein R7 and R8 are the same or different and, independently of each other, denote hydrogen, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_2$-$C_6$)-alkyl, group, an amino-($C_1$-$C_{12}$)-alkyl group, or a carbocyclic or heterocyclic, substituted or unsubstituted aromatic compound, and D denotes a sulfur atom or an oxygen atom;

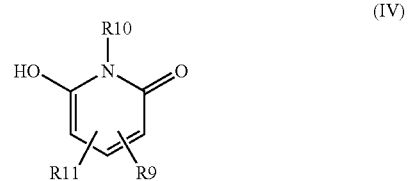
(IV)

wherein R9 denotes a hydrogen atom, a nitrile group, a ($C_1$-$C_{12}$)-alkyl group, a carbocyclic or heterocyclic aromatic compound or a (CO)—R12 carbonyl group, wherein R12 denotes hydrogen, a hydroxyl group, a ($C_1$-$C_{12}$)-alkoxy group, an amino group, a $(C_1-C_{12})$-alkylamino group, a $(C_1-C_{12})$-alkyl group, or an aryl group; and R10 and R11 are the same or different and, independently or each other, denote hydrogen, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_2-C_6)$-alkyl group, an amino-$(1-C_{12})$-alkyl group, or a carbocyclic or heterocyclic aromatic compound;

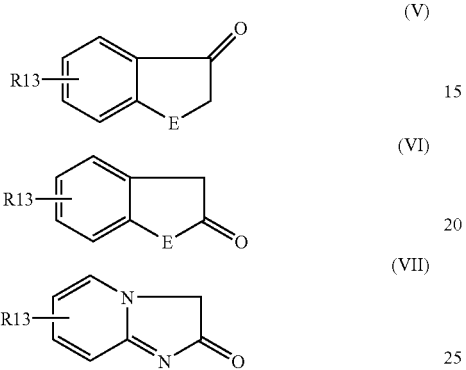

wherein E denotes an oxygen atom, a sulfur atom of an NR' amino group, with R' denoting hydrogen or a substituted or unsubstituted $(C_1-C_{12})$-alkyl group, and R13 denotes a hydrogen atom, a halogen atom, a hydroxyl group, a cyano group, a nitro group, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_1-C_6)$-alkyl group, an amino-$(C_1-C_{12})$-alkyl group, a carbocyclic or heterocyclic aromatic group, a carboxamide group, or a sulfonamide group;

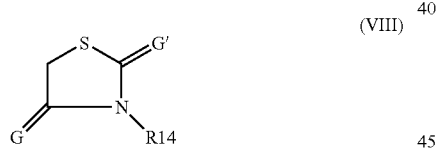

wherein G and G' are the same or different and, independently or each other, denote an oxygen atom, a sulfur atom, or an NR" amino group, with R" denoting hydrogen or a substituted or unsubstituted $(C_1-C_{12})$-alkyl group, R14 denotes hydrogen, a substituted or unsubstituted $(C_1-C_{12})$-alkyl group or a carbocyclic or heterocyclic, substituted or unsubstituted aromatic compound; and

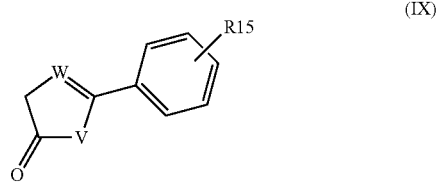

wherein V denotes an oxygen atom or an NR"' amino group, with R"' denoting hydrogen or a substituted or unsubstituted-$(C_1-C_{12})$-alkyl group; and R15 denotes a hydrogen atom, a halogen atom, a hydroxyl group, a cyano group, a nitro group, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_{1-C6})$-alkyl group, an amino-$(C_1-C_{12})$-alkyl group, a carbocyclic or heterocyclic aromatic group, a carboxamide group, or a sulfonamide group.

12. A three-component kit consisting of a first dye carrier component (A1) comprising at least one hydrazone derivative of formula (I), or a physiologically compatible salt thereof:

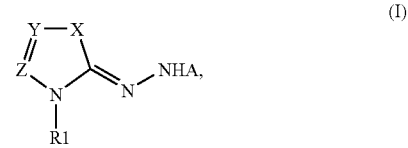

wherein X denotes oxygen, sulfur or N—R2,

Y denotes C—R3 or nitrogen, and

Z denotes C—R4 or nitrogen, provided that a heterocyclic ring in said at least one hydrazone derivative of the formula (I) contains at the most three hetero atoms;

A denotes hydrogen, an acetyl group, a trifluoroacetyl group, a formyl group, a $(C_1-C_6)$-alkyl-sulfonyl group, or an arylsulfonyl group;

R1 and R2 are the same or different and, independently of each other, denote a saturated or unsaturated $(C_1-C_{12})$-alkyl group, a halogen-substituted$(C_1-C_{12})$-alkyl group, a hydroxy-$(C_1-C_{12})$-alkyl group, an amino-$(C_1-C_{12})$-alkyl group, a sulfonic acid-$(C_1-C_{12})$-alkyl group, a formyl group, a —C(O)—$(C_1-C_{12})$-alkyl group, a substituted or unsubstituted —C(O)-phenyl group, a —C(O)NH—$(C_1-C_{12})$-alkyl group, a substituted or unsubstituted —C(O)NH-phenyl group, a substituted or unsubstituted phenyl group, or a benzyl group;

R3 and R4 are the same or different and, independently of each other, denote hydrogen. a halogen atom, a saturated or unsaturated $(C_1-C_{12})$-alkyl group, a halogen-substituted $(C_1-C_{12})$-alkyl group, a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a di$(C_1-C_{12})$-alkylamino group, a carboxyl group, a —C(O)O—$(C_1-C_{12})$-alkyl group, a substituted or unsubstituted —C(0)0-phenyl group, a substituted or unsubstituted phenyl group, or a naphthyl group;

and when Y and Z denote C—R3 and C—R4,R3 and R4 together with a remainder of the hydrazone derivative can form a heterocyclic or carbocyclic, saturated or unsaturated, substituted or unsubstituted ring system;

a second dye carrier component (A2) comprising an oxidant and at least one CH-active compound selected from the group consisting of compounds of formulas (II) to (IX) as follows:

wherein R5 denotes a cyano group, a (CO)—R6 carbonyl group, wherein R6 denotes a $(C_1-C_{12})$-alkoxy group, an amino group, a $(C_1-C_{12})$-alkylamino group, a $(C_1-C_{12})$-alkyl group or an aryl group;

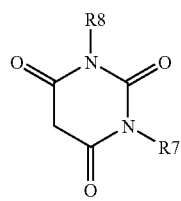

(III)

wherein R7 and R8 are the same or different and, independently of each other, denote hydrogen, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_2-C_6)$-alkyl group, an amino-$(C_1-C_{12})$-alkyl group, or a carbocyclic or heterocyclic, substituted or unsubstituted aromatic compound, and D denotes a sulfur atom or an oxygen atom;

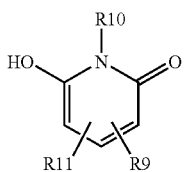

(IV)

wherein R9 denotes a hydrogen atom, a nitrile group, a $(C_1-C_{12})$-alkyl group, a carbocyclic or heterocyclic aromatic compound or a (CO)—R12 carbonyl group, wherein R12 denotes hydrogen, a hydroxyl group, a $(C_1-C_{12})$-alkoxy group, an amino group, a $(C_1-C_{12})$-alkylamino group, a $(C_1-12)$-alkyl group, or an aryl group; and R10 and R11 are the same or different and, independently or each other, denote hydrogen, a $(C_1-C_1C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_2-C_6)$-alkyl group, an amino-$(C_1-C_{12})$-alkyl group, or a carbocyclic or heterocyclic aromatic compound;

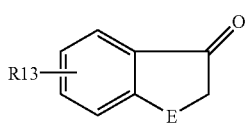

(V)

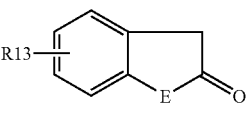

(VI)

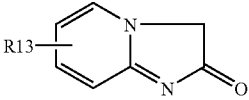

(VII)

wherein E denotes an oxygen atom, a sulfur atom of an NR' amino group, with R' denoting hydrogen or a substituted or unsubstituted $(C_1-C_{12})$-alkyl group, and R13 denotes a hydrogen atom, a halogen atom, a hydroxyl group, a cyano group, a nitro group, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_1-C_6)$-alkyl group, an amino-$(C_1-C_{12})$-alkyl group, a carbocyclic or heterocyclic aromatic group, a carboxamide group, or a sulfonamide group;

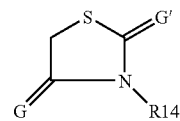

(VIII)

wherein G and G' are the same or different and, independently or each other, denote an oxygen atom, a sulfur atom, or an NR" amino group, with R" denoting hydrogen or a substituted or unsubstituted $(C_1-C_{12})$-alkyl group, R14 denotes hydrogen, a substituted or unsubstituted $(C_1-C_{12})$-alkyl group or a carbocyclic or heterocyclic, substituted or unsubstituted aromatic compound; and

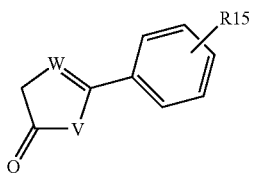

(IX)

wherein V denotes an oxygen atom or an NR'" amino group, with R'" denoting hydrogen or a substituted or unsubstituted-$(C_1-C_{12})$-alkyl group; and R15 denotes a hydrogen atom, a halogen atom, a hydroxyl group, a cyano group, a nitro group, a $(C_1-C_{12})$-alkyl group, a monohydroxy-$(C_1-C_{12})$-alkyl group, a polyhydroxy-$(C_2-C_{12})$-alkyl group, a mono-$(C_1-C_6)$-alkoxy-$(C_1-C_6)$-alkyl group, a poly-$(C_1-C_6)$-alkoxy-$(C_1-C_6)$-alkyl group, an amino-$(C_1-C_{12})$-alkyl group, a carbocyclic or heterocyclic aromatic group, a carboxamide group, or a sulfonamide group; and a third component (A3) comprising a pH adjusting agent.

13. A two-component kit consisting of
a dye carrier component (A1) consisting of a powdered dye composition, said powdered dye composition comprising
(a) at least one hydrazone derivative of formula (I), or a physiologically compatible salt thereof:

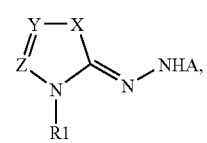

(I)

wherein X denotes oxygen, sulfur or N—R2,
Y denotes C—R3 or nitrogen, and
Z denotes C—R4 or nitrogen, provided that a heterocyclic ring in said at least one hydrazone derivative of the formula (I) contains at the most three hetero atoms;

A denotes hydrogen, an acetyl group, a trifluoroacetyl group, a formyl group, a ($C_1$-$C_6$)-alkyl-sulfonyl group, or an arylsulfonyl group;

R1 and R2 are the same or different and, independently of each other, denote a saturated or unsaturated ($C_1$-$C_{12}$)-alkyl group, a halogen-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a —C(O)—($C_1$-$C_{12}$)-alkyl group, a substituted or unsubstituted —C(0)NH-phenyl group, a —C(0)NH—($C_1$-$C_{12}$)-alkyl group, a substituted or unsubstituted —C(O)NH-phenyl group, a substituted or unsubstituted phenyl group, or a benzyl group;

R3 and R4 are the same or different, independently of each other, denote hydrogen, a halogen atom, a saturated or unsaturated ($C_1$-$C_{12}$)-alkyl group, a halogen-substituted ($C_1$-$C_{12}$)-alkyl group, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a di($C_1$-$C_{12}$)-alkylamino group, a carboxyl group, a —C(O)O—($C_1$-$C_{12}$)-alkyl group, a substituted or unsubstituted —C(O)O-phenyl group, a substituted or unsubstituted phenyl group, or a naphthyl group;

and when Y and Z denote C—R3 and C—R4, R3 and R4 together with a remainder of the hydrazone derivative can form a heterocyclic or carbocyclic, saturated or unsaturated, substituted or unsubstituted ring system;

(b) at least one OH-active compound selected from the group consisting of compounds of formulas (II) to (IX) as follows:

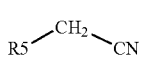
(II)

wherein R5 denotes a cyano group, a (CO)—R6 carbonyl group, wherein R6 denotes a ($C_1$-$C_{12}$)-alkoxy group, an amino group, a ($C_1$-$C_{12}$)-alkylamino group, a ($C_1$-$C_{12}$)-alkyl group or an aryl group;

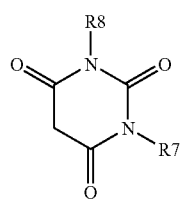
(III)

wherein R7 and R8 are the same or different and, independently of each other, denote hydrogen, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_2$-$C_6$)-alkyl group, an amino-($C_1$-$C_{12}$)-alkyl group, or a carbocyclic or heterocyclic, substituted or unsubstituted aromatic compound, and D denotes a sulfur atom or an oxygen atom;

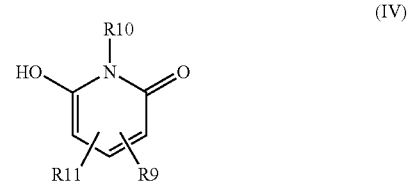
(IV)

wherein R9 denotes a hydrogen atom, a nitrile group, a ($C_1$-$C_{12}$)-alkyl group, a carbocyclic or heterocyclic aromatic compound or a (CO)—R12 carbonyl group, wherein R12 denotes hydrogen, a hydroxyl group, a ($C_1$-$C_{12}$)-alkoxy group, an amino group, a ($C_1$-$C_{12}$)-alkylamino group, a ($C_1$-$C_{12}$)-alkyl group, or an aryl group; and R10 and R11 are the same or different and, independently or each other, denote hydrogen, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_2$-$C_6$)-alkyl group, an amino-($C_1$-$C_{12}$)-alkyl group, or a carbocyclic or heterocyclic aromatic compound;

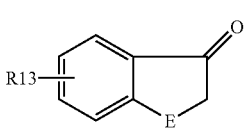
(V)

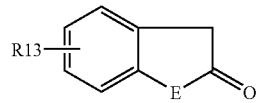
(VI)

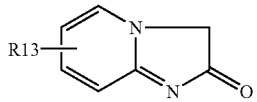
(VII)

wherein E denotes an oxygen atom, a sulfur atom of an NR' amino group, with R' denoting hydrogen or a substituted or unsubstituted ($C_1$-$C_{12}$)-alkyl group, and R13 denotes a hydrogen atom, a halogen atom, a hydroxyl group, a cyano group, a nitro group, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_1$-$C_6$)-alkyl group, an amino-($C_1$-$C_{12}$)-alkyl group, a carbocyclic or heterocyclic aromatic group, a carboxamide group, or a sulfonamide group;

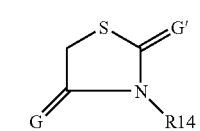
(VIII)

wherein G and G' are the same or different and, independently or each other, denote an oxygen atom, a sulfur atom, or an NR' amino group, with R' denoting hydrogen or a substituted or unsubstituted ($C_1$-$C_{12}$)-alkyl group, R14 denotes hydrogen, a substituted or unsubstituted ($C_1$-$C_{12}$)-alkyl group or a carbocyclic or heterocyclic, substituted or unsubstituted aromatic compound; and

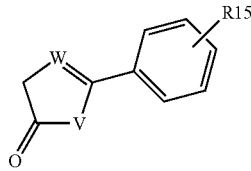

(IX)

wherein V denotes an oxygen atom or an NR''' amino group, with R''' denoting hydrogen or a substituted or unsubstituted- ($C_1$-$C_{12}$)-alkyl group; and R15 denotes a hydrogen atom, a halogen atom, a hydroxyl group, a cyano group, a nitro group, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_1$-$C_6$)-alkyl group, an amino-($C_1$-$C_2$)-alkyl group, a carbocyclic or heterocyclic aromatic group, a carboxamide group, or a sulfonamide group;

(c) at least one oxidant; and (d) optionally other powdered cosmetic additives; and a liquid cosmetic component (A2).

14. A three-component kit consisting of a first dye carrier component (A1) comprising at least one hydrazone derivative of formula (I), or a physiologically compatible salt thereof:

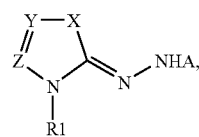

(I)

wherein X denotes oxygen, sulfur or N—R2,

Y denotes C—R3 or nitrogen, and

Z denotes C—R4 or nitrogen, provided that a heterocyclic ring in said at least one hydrazone derivative of the formula (I) contains at the most three hetero atoms;

A denotes hydrogen, an acetyl group, a trifluoroacetyl group, a formyl group, a ($C_1$-$C_6$)-alkyl-sulfonyl group, or an arylsulfonyl group;

R1 and R2 are the same or different and indepnendently of each other, denote a saturated or unsaturated ($C_1$-$C_{12}$)-alkyl group, a halogen-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a —C(O)—($C_1$-$C_{12}$)-alkyl group, a substituted or unsubstituted —C(O)-phenyl group, a —C(O)NH—($C_1$-$C_{12}$)-alkyl group, a substituted or unsubstituted —C(O)NH-phenyl group, a substituted or unsubstituted phenyl group, or a benzyl group;

R3 and R4 are the same or different and, independently of each other, denote hydrogen, a halogen atom, a saturated or unsaturated ($C_1$-$C_2$)-alkyl group, a halogen-substituted ($C_1$-$C_{12}$)-alkyl group, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a di($C_1$-$C_{12}$)-alkylamino group, a carboxyl group, a —C(O)O—($C_1$-$C_{12}$)-alkyl group, a substituted or unsubstituted —C(O)O-phenyl group, a substituted or unsubstituted phenyl group, or a naphthyl group;

and when Y and Z denote C—R3 and C—R4, R3 and R4 together with a remainder of the hydrazone derivative can form a heterocyclic or carbocyclic, saturated or unsaturated, substituted or unsubstituted ring system;

a second dye carrier component (A2) comprising at least one OH-active compound selected from the group consisting of compounds of formulas (II) to (IX) as follows:

(II)

wherein R5 denotes a cyano group, a (CO)—R6 carbonyl group, wherein R6 denotes a ($C_1$-$C_{12}$)-alkoxy group, an amino group, a ($C_1$-$C_{12}$)-alkylamino group, a ($C_1$-$C_{12}$)-alkyl group or an aryl group;

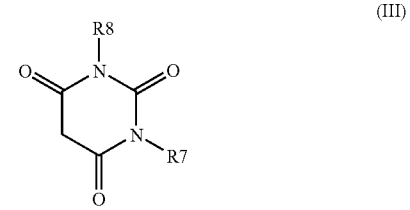

(III)

wherein R7 and R8 are the same or different and, independently of each other, denote hydrogen, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)alkyl group, a poly-($C_1$-$C_6$)-alkoxy-($C_2$-$C_6$)-alkyl group, an amino-($C_1$-$C_{12}$)-alkyl group, or a carbocyclic or heterocyclic, substituted or unsubstituted aromatic compound, and D denotes a sulfur atom or an oxygen atom;

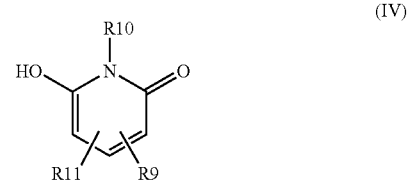

(IV)

wherein R9 denotes a hydrogen atom, a nitrile group, a ($C_1$-$C_{12}$)-alkyl group, a carbocyclic or heterocyclic aromatic compound or a (CO)—R12 carbonyl group, wherein R12 denotes hydrogen, a hydroxyl group, a ($C_1C_{12}$)-alkoxy group, an amino group, a ($C_1$-$C_{12}$)-alkylamino group, a ($C_1$-$C_{12}$)-alkyl group, or an aryl group; and R10 and R11 are the same or different and, independently or each other, denote hydrogen, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_2$-$C_6$)-alkyl group, an amino-($C_{1-12}$)-alkyl group, or a carbocyclic or heterocyclic aromatic compound;

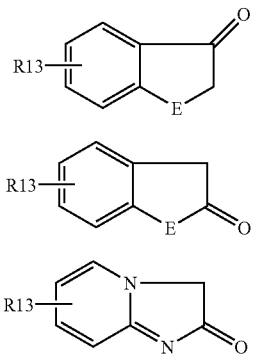

wherein E denotes an oxygen atom, a sulfur atom of an NR' amino group, with R' denoting hydrogen or a substituted or unsubstituted ($C_1$-$C_{12}$)-alkyl group, and R13 denotes a hydrogen atom, a halogen atom, a hydroxyl group, a cyano group, a nitro group, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_1$-$C_6$)-alkyl group, an amino-($C_1$-$C_{12}$)-alkyl group, a carbocyclic or heterocyclic aromatic group, a carboxamide group, or a sulfonamide group;

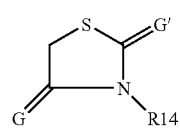

wherein G and G' are the same or different and, independently or each other, denote an oxygen atom, a sulfur atom, or an NR" amino group, with R" denoting hydrogen or a substituted or unsubstituted ($C_1$-$C_{12}$)-alkyl group, R14 denotes hydrogen, a substituted or unsubstituted ($C_1$-$C_{12}$)-alkyl group or a carbocyclic or heterocyclic, substituted or unsubstituted aromatic compound; and

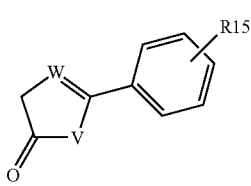

wherein V denotes an oxygen atom or an NR''' amino group, with R''' denoting hydrogen or a substituted or unsubstituted-($C_1$-$C_{12}$)-alkyl group; and R15 denotes a hydrogen atom, a halogen atom, a hydroxyl group, a cyano group, a nitro group, a ($C_1$-$C_{12}$)-alkyl group, a monohydroxy-($C_1$-$C_{12}$)-alkyl group, a polyhydroxy-($C_2$-$C_{12}$)-alkyl group, a mono-($C_1$-$C_6$)-alkoxy-($C_1$-$C_6$)-alkyl group, a poly-($C_1$-$C_6$)-alkoxy-($C_1$-$C_6$)-alkyl group, an amino-($C_1$-$C_{12}$)-alkyl group, a carbocyclic or heterocyclic aromatic group, a carboxamide group, or a sulfonamide group; and a third component (A3) comprising an oxidant.

15. A method of coloring hair, said method comprising the steps of:

a) applying a ready-to-use colorant for coloring hair to the hair;

b) allowing the ready-to-use colorant applied to the hair in step a) to act on the hair for an exposure time of 5 to 60 minutes at a temperature from 20 to 50° C.;

c) after the exposure time of 5 to 60 minutes, rinsing the hair with water and optionally washing the hair with a shampoo; and d) subsequently drying the hair;

wherein said ready-to-use colorant contains at least one hydrazone derivative of formula (I), or a physiologically compatible salt thereof:

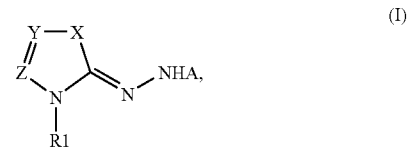

wherein X denotes oxygen, sulfur or N—R2,

Y denotes C—R3 or nitrogen, and

Z denotes C—R4 or nitrogen, provided that a heterocyclic ring in said at least one hydrazone derivative of the formula (I) contains at the most three hetero atoms;

A denotes hydrogen, an acetyl group, a trifluoroacetyl group, a formyl group, a ($C_1$-$C_6$)-alkyl-sulfonyl group, or an arylsulfonyl group;

R1 and R2 are the same or different and, independently of each other, denote a saturated or unsaturated ($C_1$-$C_{12}$)-alkyl group, a halogen-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a —C(O)—($C_1$-$C_{12}$)-alkyl group, a substituted or unsubstituted —C(O)-phenyl group, a —C(O)NH—($C_1$-$C_{12}$)-alkyl group, a substituted or unsubstituted —C(O)NH-phenyl group, a substituted or unsubstituted phenyl group, or a benzyl group;

R3 and R4 are the same or different and, independently of each other, denote hydrogen, a halogen-sudstituted ($C_1$-$C_{12}$)-alkyl group, a ($C_1$-$C_{12}$)-alkoxy group, a cyano group, a nitro group, an amino group, a ($C_1$-$C_{12}$)-alkylamino group, a di($C_1$-$C_{12}$)-alkylamino group, a carboxyl group, a —C(O)O—($C_1$-$C_{12}$)-alkyl group, a substituted or unsubstituted —C(O)O-phenyl group, a substituted or unsubstituted phenyl group, or a naphthyl group;

and when Y and Z denote C—R3 and C—R4, R3 and R4 together with a remainder of the hydrazone derivative can form a heterocyclic or carbocyclic, saturated or unsaturated, substituted or unsubstituted ring system;

at least one OH-active compound selected from the group consisting of compounds of formulas (II) to (IX) as follows:

wherein R5 denotes a cyano group, a (CO)—R6 carbonyl group, wherein R6 denotes a $(C_1\text{-}C_{12})$-alkoxy group, an amino group, a $(C_1\text{-}C_{12})$-alkylamino group, a $(C_1\text{-}C_{12})$-alkyl group or an aryl group;

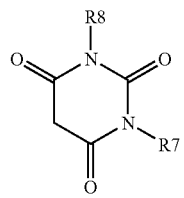

(III)

wherein R7 and R8 are the same or different and, independently of each other, denote hydrogen, a $(C_1\text{-}C_{12})$-alkyl group, a monohydroxy-$(C_1\text{-}C_{12})$-alkyl group, a polyhydroxy-$(C_2\text{-}C_{12})$-alkyl group, a mono-$(C_1\text{-}C_6)$-alkoxy-$(C_1\text{-}C_6)$-alkyl group, a poly-$(C_1\text{-}C_6)$-alkoxy-$(C_2\text{-}C_6)$-alkyl group, an amino-$(C_1\text{-}C_{12})$-alkyl group, or a carbocyclic or heterocyclic, substituted or unsubstituted aromatic compound, and D denotes a sulfur atom or an oxygen atom;

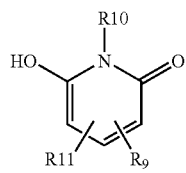

(IV)

wherein R9 denotes a hydrogen atom, a nitrile group, a $(C_1\text{-}C_{12})$-alkyl group, a carbocyclic or heterocyclic aromatic compound or a (CO)—R12 carbonyl group, wherein R12 denotes hydrogen, a hydroxyl group, a $(C_1\text{-}C_{12})$-alkoxy group, an amino group, a $(C_1\text{-}C_{12})$-alkylamino group, a $(C_1\text{-}C_{12})$-alkyl group, or an aryl group; and
R10 and R11 are the same or different and, independently or each other, denote hydrogen, a $(C_1\text{-}C_{12})$-alkyl group, a monohydroxy-$(C_1\text{-}C_{12})$-alkyl group, a polyhydroxy-$(C_2\text{-}C_{12})$-alkyl group, a mono-$(C_1\text{-}C_6$-alkoxy-$(C_1\text{-}C_6$-alkyl group, a poly-$(C_1\text{-}C_6)$-alkoxy-$(C_2\text{-}C_6)$-alkyl group, an amino-$(C_1\text{-}C_{12})$-alkyl group, or a carbocyclic or heterocyclic aromatic compound;

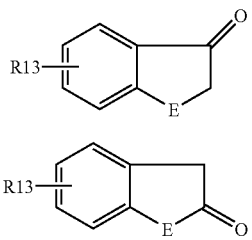

(V)

(VI)

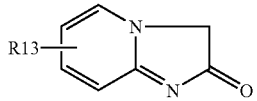

(VII)

wherein E denotes an oxygen atom, a sulfur atom of an NR' amino group, with R' denoting hydrogen or a substituted or unsubstituted $(C_1\text{-}C_{12})$-alkyl group, and
R13 denotes a hydrogen atom, a halogen atom, a hydroxyl group, a cyano group, a nitro group, a $(C_1\text{-}C_{12})$-alkyl group, a monohydroxy-$(C_1\text{-}C_{12})$-alkyl group, a polyhydroxy-$(C_2\text{-}C_{12})$-alkyl group, a mono-$(C_1\text{-}C_6)$-alkoxy-$(C_1\text{-}C_6)$-alkyl group, a poly-$(C_1\text{-}C_6)$-alkoxy-$(C_1\text{-}C_6)$-alkyl group, an amino-$(C_1\text{-}C_{12})$-alkyl group, a carbocyclic or heterocyclic aromatic group, a carboxamide group, or a sulfonamide group;

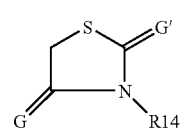

(VIII)

wherein G and G' are the same or different and, independently or each other, denote an oxygen atom, a sulfur atom, or an NR" amino group, with R" denoting hydrogen or a substituted or unsubstituted $(C_1\text{-}C_{12})$-alkyl group,
R14 denotes hydrogen, a substituted or unsubstituted $(C_1\text{-}C_{12})$-alkyl group or a carbocyclic or heterocyclic, substituted or unsubstituted aromatic compound; and

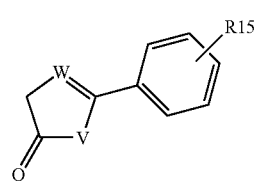

(IX)

wherein V denotes an oxygen atom or an NR''' amino group, with R''' denoting hydrogen or a substituted or unsubstituted-$(C_1\text{-}C_{12})$-alkyl group; and
R15 denotes a hydrogen atom, a halogen atom, a hydroxyl group, a cyano group, a nitro group a, $(C_1\text{-}C_{12})$-alkyl group, a monohydroxy-$(C_1\text{-}C_{12})$-alkyl group, a polyhydroxy-$(C_2\text{-}C_{12})$-alkyl group, a mono-$(C_1\text{-}C_6)$-alkoxy-$(C_1\text{-}C_6)$-alkyl group, a poly-$(C_1\text{-}C_6)$-alkoxy-$(C_1\text{-}C_6)$-alkyl group, an amino-$(C_1\text{-}C_{12})$-alkyl group, a carbocyclic or heterocyclic aromatic group, a carboxamide group, or a sulfonamide group; and
at least one oxidant.

* * * * *